United States Patent
Stein et al.

(10) Patent No.: US 9,133,120 B2
(45) Date of Patent: Sep. 15, 2015

(54) FENTANYL DERIVATIVES AS PH-DEPENDENT OPIOID RECEPTOR AGONISTS

(75) Inventors: Christoph Stein, Berlin (DE); Marcus Weber, Berlin (DE); Christian Zöllner, Hamburg (DE); Olga Scharkoi, Berlin (DE)

(73) Assignees: CHARITÉ—UNIVERSITÄTSMEDIZIN BERLIN, Berlin (DE); KONRAD-ZUSE-INSTITUT, Berlin (DE)

( * ) Notice: Subject to any disclaimer, the term of this patent is extended or adjusted under 35 U.S.C. 154(b) by 0 days.

(21) Appl. No.: 14/239,461

(22) PCT Filed: Aug. 17, 2012

(86) PCT No.: PCT/EP2012/066071
§ 371 (c)(1),
(2), (4) Date: Mar. 5, 2014

(87) PCT Pub. No.: WO2013/026787
PCT Pub. Date: Feb. 28, 2013

(65) Prior Publication Data
US 2014/0228406 A1    Aug. 14, 2014

(30) Foreign Application Priority Data
Aug. 19, 2011    (EP) .................................. 11178122

(51) Int. Cl.
*A61K 31/445*    (2006.01)
*C07D 211/58*    (2006.01)

(52) U.S. Cl.
CPC .................................. *C07D 211/58* (2013.01)

(58) Field of Classification Search
CPC .................................................... C07D 211/58
USPC .......................................... 514/329; 546/224
See application file for complete search history.

(56) References Cited

U.S. PATENT DOCUMENTS 3,923,992 A    12/1975    Riley et al.
6,677,332 B1 *  1/2004    Cuny et al. ............... 514/212.02

OTHER PUBLICATIONS

Casy et al. "Structure-act . . . " J. Pharm. Pharmacol. vo. 40 (5), p. 605-608 (1987).*
Stein "Opioid receptors . . . " NCBI Landes Bioscience p. 1-8 (2000).*
Wakefield "Flourinated pharma . . . " Chem. Techology p. 74-78 (2003).*
Zhou et al. "Contribution of opioid . . . " J. Pharmac. Expe. Ther. vol. 286(2) p. 1000-1006 (1998).*
Bohm et al. "Fluorine in medicinal chem . . . " ChemBioChem v.5, p. 637-643 (2004).*
Fehrenbach et al. "Dental hygiene" p. 473 (2008.*
Punnia "Evaluation of pH . . . " J. Oral Patho. 16(1) p. 36-44 (1987).*
Roche "Improveing pharma . . . " Am. J. Pharm. Edu. 71(6) article 122 p. 1-15 (2007).*
Hwang, D.-R. et al. 1986 "Synthesis and evaluation of fluorinated derivatives of fentanyl as candidates for opiate receptor studies using positron emission tomography" *Journal of Labelled Compounds and Radiopharmaceuticals* 23: 277-293.
Maryanoff, B.E. et al. 1982 "Potential affinity labels for the opiate receptor based on fentanyl and related compounds" *Journal of Medicinal Chemistry* 25: 913-919.
Patani, G.A. et al. 1996 "Bioisosterism: A Rational Approach in Drug Design" *Chemical Reviews* 96: 3147-3176.

* cited by examiner

*Primary Examiner* — Celia Chang
(74) *Attorney, Agent, or Firm* — Knobbe, Martens, Olson & Bear, LLP

(57) ABSTRACT

The invention relates to fluorinated fentanyl derivatives that function as opioid receptor agonists, which activate target opioid receptors in a pH-dependent manner, and are thus selective for the receptors in inflamed (acidic) milieu; uses thereof and pharmaceutical compositions comprising them.

9 Claims, 10 Drawing Sheets

Figure 1:
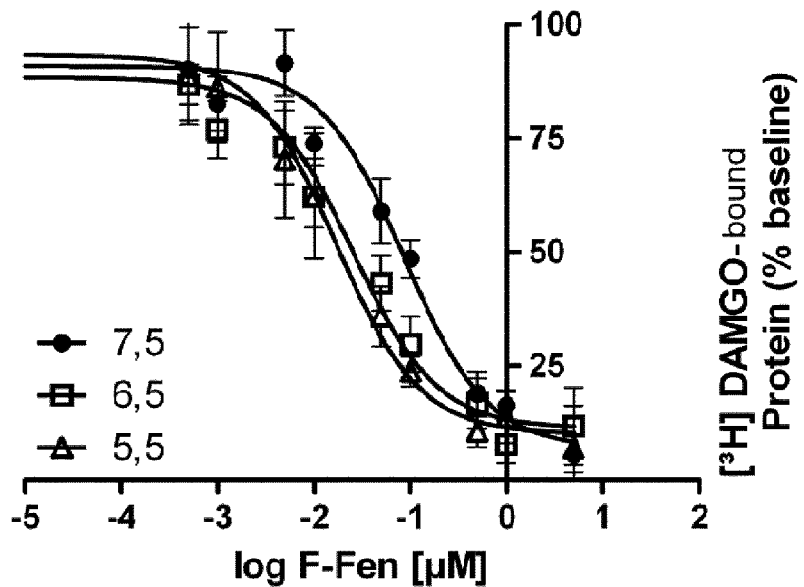
Figure 1:
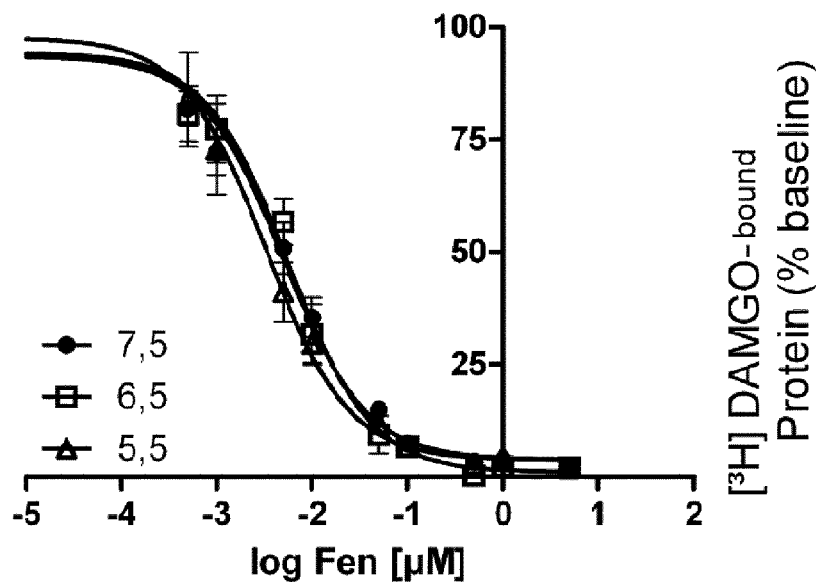

Synthesis outline:

Step 1:

Cyclohexane // Ethylacetate 10:1// KMnO₄

Reactant          Product

Step 2:

Cyclohexane // Ethylacetate 10:1// KMnO$_4$

Reactant      Product

Cyclohexane // Ethylacetate 10:1// KMnO$_4$

Product

Step 3:

Cyclohexane // Ethylacetate 3:1// UV and KMnO$_4$

◄ Product

UV      KMnO$_4$

Step 5:

Cyclohexane // Ethylacetate 3:1// KMnO$_4$ / UV

◄ Product

RG

Step 6:

Cyclohexane // Ethylacetate 1:2 // UV / KMnO$_4$

◄ only UV

◄ only KMnO$_4$

RG

FENTANYL DERIVATIVES AS PH-DEPENDENT OPIOID RECEPTOR AGONISTS

DESCRIPTION

The invention relates to compounds (fentanyl derivates) that function as opioid receptor agonists, which activate target opioid receptors in a pH-dependent manner, uses thereof and pharmaceutical compositions comprising said compounds.

BACKGROUND OF THE INVENTION

The use of currently available opioid analgesics is limited by major adverse side effects such as drowsiness, respiratory depression, constipation, tolerance or addiction. Following painful peripheral tissue injury and inflammation, opioid receptors on peripheral terminals of primary sensory neurons are upregulated, their G-protein coupling, signaling and recycling is enhanced, and their activation results in potent inhibition of neuronal excitability and analgesia. The augmented intracellular signaling suggests conformational alterations of opioid receptors or ligands in the inflamed environment. Systemically applied conventional opioid agonists (e.g. morphine) activate both peripheral and central opioid receptors. Agonists at central opioid receptors lead primarily to severe side effects, leaving a significant need in the field of pain treatment for compounds that work preferably selectively on peripheral receptors.

Inflammation, accompanied by tissue acidosis, is an essential component of a large group of painful syndromes (Stein, C. et al. Brain Res Rev 60, 90-113 (2009)), including arthritis, skin inflammation, inflammatory back pain, headache (certain types of neurogenic migraine), inflammatory lesions of the central and peripheral nervous system (neuropathic pain), cancer pain, disorders of the immune system (HIV/AIDS, multiple sclerosis), traumatic and postoperative pain. Currently available analgesic drugs are limited by unacceptable side effects such as the central actions of opioids (e.g. sedation, respiratory depression, nausea, addiction, tolerance), the intestinal effects of opioids (constipation, ileus), the gastrointestinal and cardiovascular effects of cyclooxygenase (COX) inhibitors (e.g. bleeding, ulcers, thrombo-embolic complications) and the adverse effects of anticonvulsants and antidepressants (e.g. sedation, ataxia, arrhythmias, coronary vasoconstriction). Therefore, there is need of development of new generations and formulations of opioids which are devoid of these side effects but retain clinical efficacy.

This can be achieved by targeting opioid receptors on peripheral terminals of dorsal root ganglion (DRG) neurons (also called nociceptors or primary sensory neurons) through the local application of exogenous, or the release of endogenous opioids within injured tissue. Moreover, a large proportion (50-100%) of the antinociceptive effects produced by systemically administered opioids can be mediated by such peripheral opioid receptors, and opioid agonists that do not readily enter the central nervous system (CNS) can have the same analgesic efficacy as conventional opioids (Stein, C. et al. Pharmacol Rev 2011;63:860-881), Craft, R. M., et al., J Pharmacol Exp Ther 1995; 275:1535-42, amongst others). In addition, peripherally acting opioids have been shown to reduce inflammation by modulating proinflammatory mediators, edema, plasma extravasation and other parameters (Stein, C. et al. Curr Pharm Design 2012, PMID: 22747536). However, despite the fact that peripherally acting opioids have been shown to reduce inflammation, leading to potential success in pain relief strategies regarding modulation of peripheral receptors, few methods have been disclosed for effectively targeting selectively peripheral opioid receptors without effects on either the gut or CNS.

Opioid pharmacology commands a huge armamentarium of non-peptidic and peptidic opioid receptor ligands. The most thoroughly studied include the alkaloid morphine, the piperidine fentanyl, and the enkephalin derivative (D-Ala$^2$, N-MePhe$^4$,Gly$^5$-ol)-enkephalin (DAMGO). All of these bind to the mu-receptor, the most important receptor type for the mediation of analgesic effects in animals and humans (Zöllner, C. and Stein, C. Handbook of Experimental Pharmacology 2007; Vol. 177 Analgesia). Chemical modification of such compounds has been accomplished manifold and has produced highly selective ligands for each receptor type as well as agonists that do not enter the CNS. While the latter can induce potent antinociception without central side effects, they are still likely to activate opioid receptors in the gut (when applied orally or systemically), which commonly results in the occurrence of constipation or vomiting. Therefore, it is necessary to develop opioid receptor-ligands with a particular focus on specific activity in the environment in damaged (inflamed) tissue.

Fentanyl is a potent synthetic opioid ("narcotic") analgesic with a rapid onset and short duration of action. It is a potent agonist at mu-opioid receptors. Historically it has been used to treat chronic and breakthrough pain and is commonly used before, during and after procedures as a pain reliever as well as an anaesthetic. However, fentanyl can exhibit significant side effects, such as nausea, vomiting, constipation, dry mouth, somnolence, confusion, hypoventilation, apnoea, tolerance and addiction, in addition to abdominal pain, headache, fatigue, weight loss, dizziness, nervousness, hallucination, anxiety, depression, flu-like symptoms, dyspepsia (indigestion), and urinary retention, which renders fentanyl in many cases unusable, especially when delivered systemically to a subject in pain.

Structural derivatives of fentanyl have been disclosed in the prior art. Maryanoff et al (Journal of Medicinal Chemistry, 25:8, 913-919) and Riley et al (U.S. Pat. No. 3,923,992) disclose methyl-fentanyl derivatives that exhibit a methyl group at the so-called "3-position" of fentanyl. The modification of fentanyl with the methyl substituent leads to enhanced binding to opioid receptors, which enables—according to the prior art—the possibility of isolation of ligand-bound opioid receptors via affinity labelling methods (Maryanoff et al) in addition to pharmaceutical use of the derivative as an analgesic (Riley et al). Furthermore, fluor-fentanyl derivatives have been disclosed in the prior art that were intended for use in studies on opioid receptors using positron emission tomography (Hwang et al, Journal of Labelled Compounds and Radiopharmaceuticals, 23:3, 277-293). The fluor-fentanyl derivatives disclosed therein exhibit an F atom attached to the phenyl ring (not adjacent to the amide group) of fentanyl. Hwang et al report a reduction in binding strength to an opioid receptor and a reduction in analgesic effect of the fluor-fentanyl derivative compared to fentanyl itself. Importantly, none of these derivatives aimed at or generated compounds that selectively bind and activate peripheral opioid receptors in inflamed (acidic) milieu, in contrast to the present application (see below).

Despite attempts at generating fentanyl derivatives that demonstrate improved binding to opioid receptors (in normal, nonacidic milieu) and associated improvements in analgesic effect, there remains a significant need in the art to develop fentanyl derivatives that do not exhibit the side effects commonly associated with fentanyl and other conventional opioid compounds (e.g. morphine). Many of these side effects are known to be associated with the effect of such compounds on the CNS.

The mechanisms underlying the peripheral antinociceptive effects of opioids have been investigated in animals and humans (Stein, C., et al., Nat Med 9, 1003-8 (2003); Pharmacol Rev 2011;63:860-881). To this end, Freund's adjuvant (CFA)-induced hind paw inflammation in rodents has been studied, in addition to the peripheral application of small, systemically inactive doses of morphine in patients undergoing surgery or suffering from chronic arthritis. In several controlled clinical studies the inventors and others have shown that intraarticular morphine produces pain relief of similar efficacy to local anesthetics or steroids without systemic or local side effects. Such effects are apparently mediated by opioid receptors localized on peripheral terminals of DRG neurons. The activation of these receptors reduces neuronal excitability, nociceptive impulse propagation and proinflammatory neuropeptide release. In particular, it has been shown that opioid agonists inhibit the TRPV1 ion channel, which is preferentially expressed in DRG neurons and is activated by the pungent compound capsaicin, protons and other stimuli. The inhibition occurs via opioid receptor-coupled $G_{i/o}$ proteins and the cAMP pathway. Furthermore, it has been shown that peripherally mediated opioid anti-nociception is particularly prominent within inflamed tissue, and that its efficacy increases with the duration of the inflammatory process. Underlying mechanisms include upregulation of synthesis, peripherally directed axonal transport and G-protein coupling of opioid receptors in DRG neurons.

Importantly, pH values as low as 4-5 have been measured in painful inflammation (Reeh, P. W. & Steen, K. H., Prog Brain Res 113, 143-51 (1996), Woo, Y. C., et al., Anesthesiology 101, 468-75 (2004). This significant change in pH in inflamed tissue provides a potential mechanism according to which inflammation-specific active agents can be developed, which only exhibit an opioid receptor agonistic function in the area of damage, inflammation and/or pain. The present invention is related to the influence of an inflamed (acidic) environment on opioid receptor-ligand interactions and provides ligands that selectively activate opioid receptors in injured (acidic, low pH) tissue. The agonists provided herein have been demonstrated to exhibit analgesic activity in animal models of inflammatory pain in vivo. The compounds disclosed herein and methods of pharmaceutical application transcend traditional concepts and methods of pain treatment relating to specific activation of peripheral opioid receptors. The present invention therefore relates to the influence of an inflamed (acidic) environment on opioid receptor-ligand interactions and provides ligands that selectively activate opioid receptors in injured tissue.

SUMMARY OF THE INVENTION

In light of the prior art, the technical problem underlying the present invention is to provide compounds or substances that selectively activate opioid receptors in injured tissue, thereby avoiding common side effects associated with activation of opioid receptors in the CNS or gut.

This problem is solved by the features of the independent claims. Preferred embodiments of the present invention are provided by the dependent claims.

Therefore, an object of the invention is to provide compounds of the general Formula I

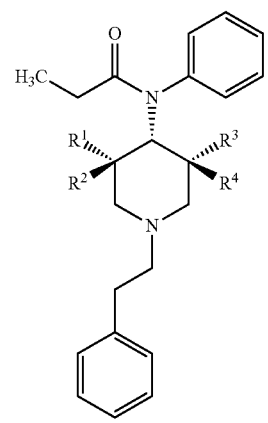

Formula I whereby at least one of R1, R2, R3, R4 is F (fluorine), and the remaining residues at positions R1, R2, R3, R4 are H (hydrogen).

In a preferred embodiment of the present invention the compound as described herein is selected from the group comprising of:

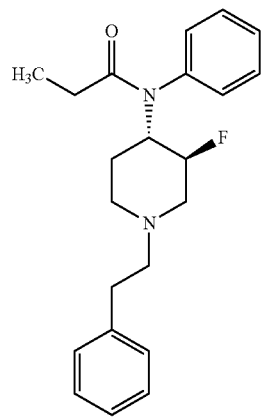

Formula II

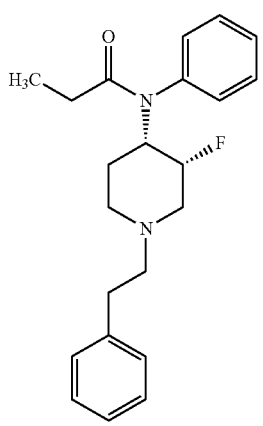

Formula III

-continued

Formula IV

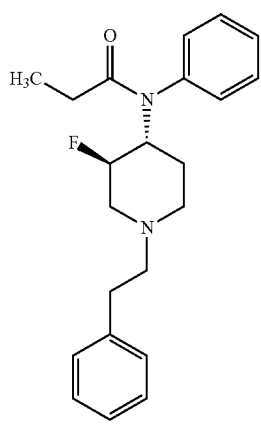

Formula V

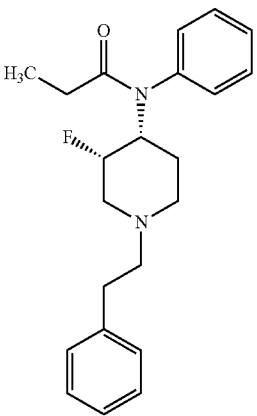

In one embodiment of the present invention the compound as described herein is characterized in that said compound is an opioid receptor agonist that activates target opioid receptor in a pH-dependent manner.

In one embodiment of the present invention the compound as described herein is characterized in that activation of said receptor by the compound occurs selectively at pH values of 4, 4.5, 5, 5.5, 6 or 6.5, or any other pH value below 7.

In one embodiment of the present invention the compound as described herein is characterized in that said compound exhibits a pKa value between 4 and 7, preferably between 4.5 and 6.5, more preferably between 5 and 6. A further preferred embodiment relates to an F-fentanyl derivative as described herein with a pKa value between 5.5 and 6.5, for example 6, or more preferably 6.2.

In one embodiment of the present invention the compound as described herein is characterized in that said compound comprises a protonated N-group. In a preferred embodiment the compound is characterized in that the candidate compound exhibits an N group which can be protonated or non-protonated, whereby a protonated N group occurs in candidate compounds of pKa<7 when under conditions of pH<7, and the compound exhibiting a protonated N group activates said target opioid receptor.

In one embodiment of the present invention the compound as described herein is characterized in that said target opioid receptor is selected from the group comprising of the mu-receptor, delta-receptor and kappa-receptor. The opioid receptors mu (μ), delta (δ) and kappa (κ) are partially redundant in function and are intended as target opioid receptors according to the present invention. This includes the subtypes of the $\mu_1$, $\mu_2$, $\mu_3$, $\delta_1$, $\delta_2$, $\kappa_1$, $\kappa_2$ and $\kappa_3$ receptors.

In one embodiment of the present invention the compound as described herein is characterized in that the compound activates the target opioid receptor in conditions of inflammation-associated pH, preferably low pH, or preferably low physiological pH values in inflamed tissue, preferably at pH values of 4, 4.5, 5, 5.5, 6 or 6.5, or any other pH value below 7.

In one embodiment of the present invention the compound as described herein is characterized in that the compound activates opioid receptors at the terminals of peripheral sensory neurons.

In one embodiment of the present invention the compound as described herein is characterized in that the compound exhibits inflammation-specific peripheral analgesic function in inflamed or injured tissues without causing central or intestinal effects.

The invention further relates to the compound as described herein for use as a medicament.

In a preferred embodiment the compound of the present invention is intended for use as a medicament in the treatment of inflammation-associated pain, preferably arthritis, skin inflammation, inflammatory back pain, headache (including neurogenic migraine), inflammatory lesions of the central and peripheral nervous system (neuropathic pain), cancer pain, disorders of the immune system (HIV/AIDS, multiple sclerosis), traumatic pain, postoperative pain, inflamed joints, dental surgery, visceral pain, bone pain, burn injury and/or eye lesions.

A further aspect of the invention relates to the compound as described herein for use as a medicament in activating peripheral opioid receptors in the treatment of pain in injured or inflamed tissue.

A further aspect of the invention relates to a pharmaceutical composition comprising the compound of the present invention, and/or salts, derivatives and/or stereoisomers thereof, together with at least one pharmaceutically acceptable carrier.

In a preferred embodiment the pharmaceutical composition as described herein comprises of a mixture of at least 2 compounds according to formulae II, III, IV and/or V, and/or salts, derivatives and/or stereoisomers thereof, preferably comprising a stereoisomeric mixture of compounds according to formulae II, III, IV and/or V.

The pharmaceutical composition of the present invention is preferably prepared for systemic, oral and/or local application, preferably in tablet form or in a form suitable for injection.

A further aspect of the invention relates to a method for the treatment of inflammatory pain comprising the administration of a therapeutically relevant amount of the compound and/or the pharmaceutical composition as described herein to a human subject. The invention further encompasses the use of the compounds of the present invention in a method of treatment, in addition to the use of the compounds to achieve the biological effects obtained herein, either in vivo or in vitro, such as target opioid receptor activation in conditions of low pH, preferably at pH values associated with inflammation.

DETAILED DESCRIPTION OF THE INVENTION

The invention relates to fentanyl derivatives that function as opioid receptor agonists, which activate target opioid receptors in a pH-dependent manner. The compounds as described herein relate to improved and/or alternative derivatives to the fentanyl compounds known in the art. The fluoro-substituents at positions R1, R2, R3, R4 exhibit an enhanced electronegativity when compared to hydrogen and therefore lead to an enhanced electronegativity of the fentanyl derivative molecule, thus providing the claimed compounds with their inventive properties as described. Through the specific fluor-modification of the fentanyl backbone disclosed herein the overall conformation or three-dimensional structure of the molecules remains unchanged, or only changed to a minor extent, whereas the electronegativity is significantly reduced.

Importantly, the fentanyl derivatives disclosed in the prior art do not exhibit the desired combination of structural and physical features required for the (pH-dependent) efficacy shown by the compounds of the present invention. Methyl derivatives as disclosed in the art do not produce the required reduction in pKa of the fentanyl compound in order to enable inflammation-related pH-specific activity. The electronegativity of F in comparison to C is significantly larger, providing a significant difference in pKa of the molecule. The previously disclosed fluor-fentanyl derivatives either do not reduce the pKa of the compounds significantly and/or lead to a disadvantageous structural modification, so that the desired analgesic activity does not occur. The compounds of the present invention therefore demonstrate a unique combination of features neither suggested not disclosed in the prior art.

To be activated, the mu-opioid receptor generally requires an opioid agonist with protonated N-group (Li et al, Life Sciences, vol. 65, 2, 175-185, 1999). The pKa value of the N-group of most conventional opioids is about 8 (e.g. 8.2 for morphine, 8.4 for fentanyl). Thus, the N-group is protonated both in inflamed (pH 5-6) and in healthy (pH 7.4) tissue and opioid receptors are activated in both environments. If the pKa value of an agonist's N-group could be decreased to about 6, it would be protonated in inflamed but deprotonated in normal tissue and, therefore, it would be active only in inflamed tissue. Therefore the replacement of hydrogen by fluorine atoms, which should have no major influence on the dynamic behavior of the opioid agonist, provides an elegant solution to the problem underlying the present invention. Fluorine is very electronegative and hence attracts protons and decreases the pKa-value.

The "pH-dependent activation" between the compounds as described herein and the opioid receptor relates to an enhanced receptor activation at pH values less than 7, in comparison to values above 7. In a preferred embodiment the receptor activation by the compound is enhanced proportionally with lowering pH values. Obviously at very low pH values the receptor protein may undergo significant conformational change and/or denaturation, so that the receptor activation no longer occurs in an improved manner. Therefore the receptor activation by F-fentanyl occurs preferably at pH values of 4, 4.5, 5, 5.5, 6 or 6.5, or any other pH value below 7, whereby the receptor activation occurs most preferentially at pH values between 5 and 6. Although some receptor activation may occur at either higher or lower pH values as explicitly provided herein, the receptor activation (and associated pain-relief in vivo) occurs most preferentially at pH levels, which are naturally lowered to approximately 4, 4.5, 5, 5.5, 6 or 6.5, or any other pH value below 7, after injury or inflammation of mammalian tissue.

The activation of the receptor occurs in a preferred embodiment via binding of the agonist to the receptor. However, the binding of the agonist to the receptor may be either a stable or transient event, of either strong or weak interaction, such that the receptor is activated preferably by agonist-receptor physical interaction.

The activation of opioid receptors by compounds as described herein relates preferably to receptor activation by compounds according to formula I and the mu receptor. However, due to structural and/or functional similarities between various opioid receptors and/or signaling pathways involved in the analgesic effect, the receptor activation by the claimed compounds may also occur with opioid receptors in addition to the mu-receptor, such as the delta-receptor, kappa-receptor, or other related opioid receptors.

The terms "inflammatory pain" and "inflammation-associated pain" are used interchangeably. Said inflammation-associated pain relates to any kind of pain experienced by a subject when inflammation is involved. The compounds of the present invention are intended for use in the treatment of arthritis, skin inflammation, inflammatory back pain, headache (including neurogenic migraine), inflammatory lesions of the central and peripheral nervous system (neuropathic pain), cancer pain, disorders of the immune system (HIV/AIDS, multiple sclerosis), traumatic pain, postoperative pain, inflamed joints, dental surgery, visceral pain, bone pain, burn injury, eye lesions. These disorders are intended as examples of conditions that are associated with inflammatory pain and are not intended as a limiting disclosure.

The compounds of the present invention exhibit the surprising advantage that unacceptable side effects of traditional analgesic treatments are avoided, such as the central actions of opioids (e.g. sedation, respiratory depression, nausea, addiction, tolerance), the intestinal effects of opioids (constipation, ileus), the gastrointestinal and cardiovascular effects of cyclooxygenase (COX) inhibitors (e.g. bleeding, ulcers, thromboembolic complications) and the adverse effects of anticonvulsants and antidepressants (e.g. sedation, ataxia, arrhythmias, coronary vasoconstriction). The compounds themselves and their inflammation-specific activity have been neither suggested nor disclosed in the prior art.

In the present invention "treatment" generally means to obtain a desired pharmacological effect and/or physiological effect. The effect may be prophylactic in view of completely or partially preventing a disease and/or a symptom, or may be therapeutic in view of partially or completely curing a disease and/or adverse effect of the disease. In the present specification, "treatment" includes arbitrary treatments of diseases in mammals, in particular, humans, for example, the following treatments (a) to (c): (a) Prevention of onset of a disease or symptom in a patient who may have a predisposition of the disease or symptom, but is not yet diagnosed to have the predisposition; (b) Inhibition of a symptom of a disease, that is, prevention of progression of the symptom; (c) Amelioration of a symptom of a disease, that is, induction of regression of the disease or symptom.

The term "pharmaceutical composition" refers to a combination of the agent as described herein with a pharmaceutically acceptable carrier. The phrase "pharmaceutically-acceptable" refers to molecular entities and compositions that do not produce a severe allergic or similar untoward reaction when administered to a human. As used herein, "carrier" includes any and all solvents, dispersion media, vehicles, coatings, diluents, antibacterial and antifungal agents, isotonic and absorption delaying agents, buffers, carrier solutions, suspensions, polymers, colloids, and the like. The use of such media and agents for pharmaceutical active substances is well known in the art. Supplementary active ingredients can also be incorporated into the compositions. A pharmaceutical composition of the present invention can include pharmaceutically acceptable salts of the components therein. The pharmaceutical composition containing the active ingredient may be in a form suitable for topical or oral use, for example, as tablets, troches, lozenges, aqueous or oily suspensions, dispersible powders or granules, emulsions, hard or soft capsules, nanocarriers, liposomes, gels, lollipops, mucosal adhesives, or syrups or elixirs. Compositions intended for topical or oral use may be prepared according to any method known to the art for the manufacture of pharmaceutical compositions and such compositions. Tablets contain the active ingredient in admixture with non-toxic pharmaceutically acceptable excipients which are suitable for the manufacture of tablets. The tablets may be uncoated or they may be coated by known techniques to delay disintegration and absorption in the gastrointestinal tract and thereby provide a sustained action over a longer period. The compounds of the present invention may also be used in pharmaceutically acceptable forms suitable for injection, leading to either local or systemic administration of the compound.

Dosage levels of approximately 0.01 mg to about 500 mg per kilogram of body weight per day are useful in the treatment of the above-indicated conditions. For example, inflammation-related pain may be effectively treated by the administration of about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration in humans may vary from about 5 to about 95% of the total composition. Dosage unit forms will generally contain between about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

FIGURES

The invention is further described by the figures. These are not intended to limit the scope of the invention.

FIG. 1. Competitive binding experiments measuring the affinity of control mu-agonists to the mu-receptor.

Figure 2:
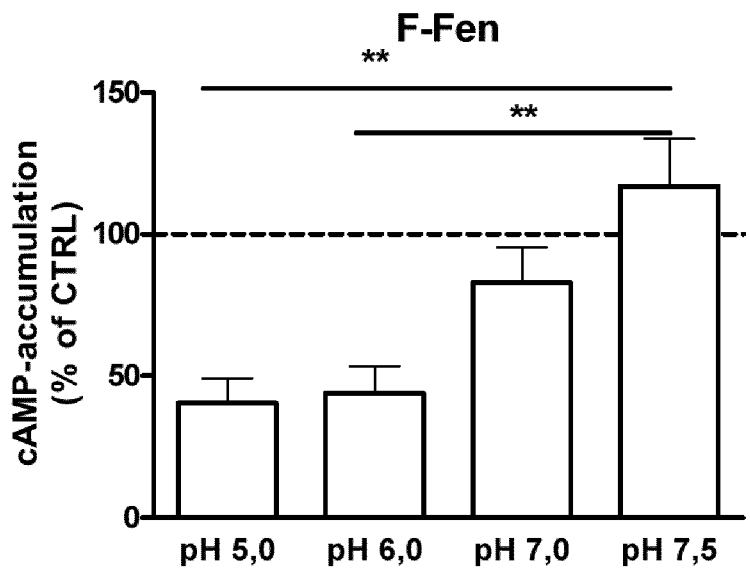
Figure 2:
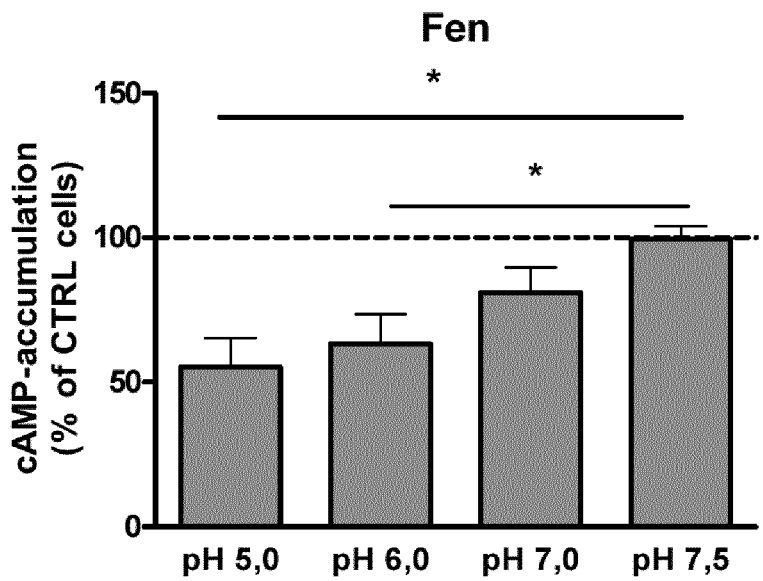

FIG. 2. Suppression of FSK/IBMX-stimulated cAMP-accumulation by F-fentanyl (white) and fentanyl (grey).

Figure 3:
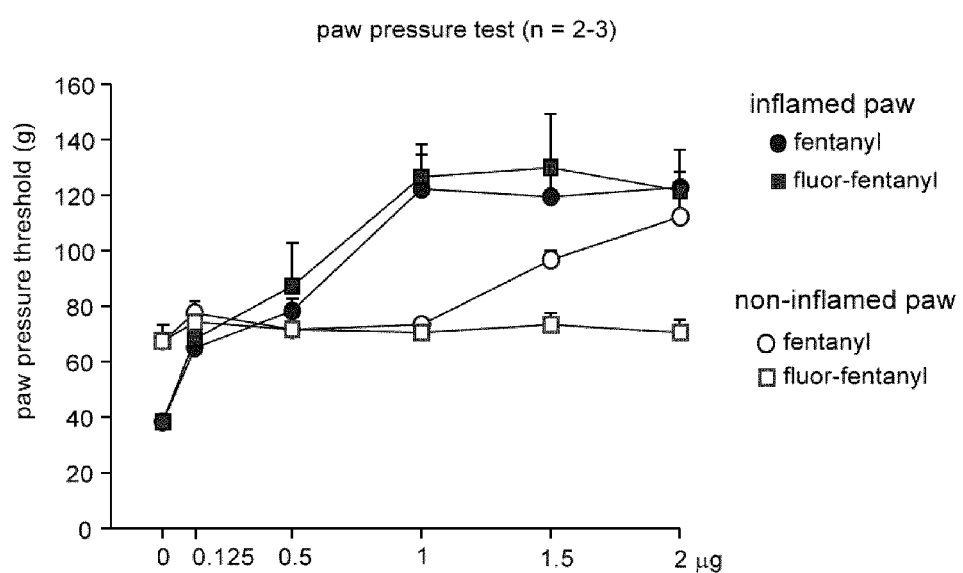

FIG. 3. Fluor-fentanyl reduces mechanical pain-sensitivity (hyperalgesia) after intraplantar injection in rats.

Figure 4:
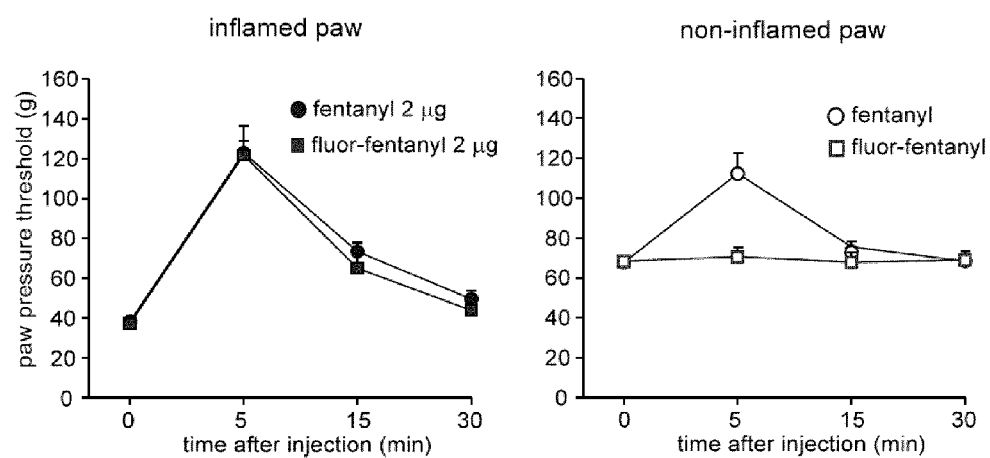

FIG. 4. Time-course of intraplantar fluor-fentanyl-induced analgesia.

Figure 5:
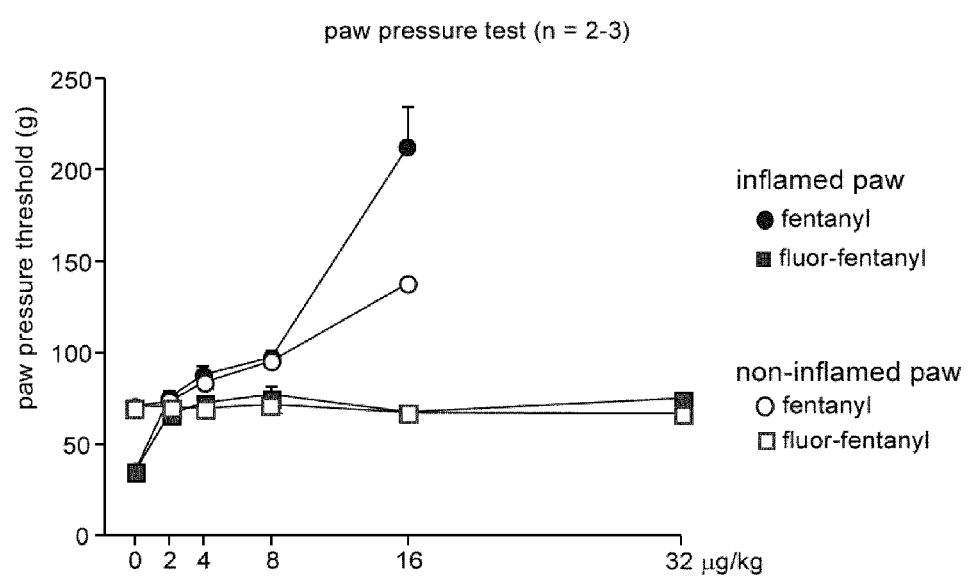

FIG. 5. Fluor-fentanyl reduces mechanical hyperalgesia after intravenous injection in rats. It has no effect on contralateral noninflamed paws, does not produce respiratory depression or sedation (even at high doses of 16-32 µg/kg), indicating a lack of central actions.

Figure 6:
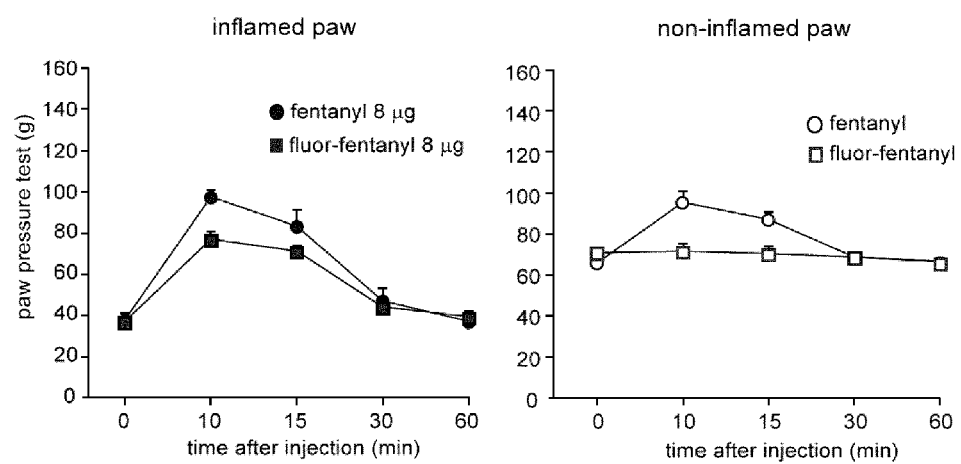

FIG. 6. Time-course of intravenous fluor-fentanyl-induced analgesia.

Figure 7:
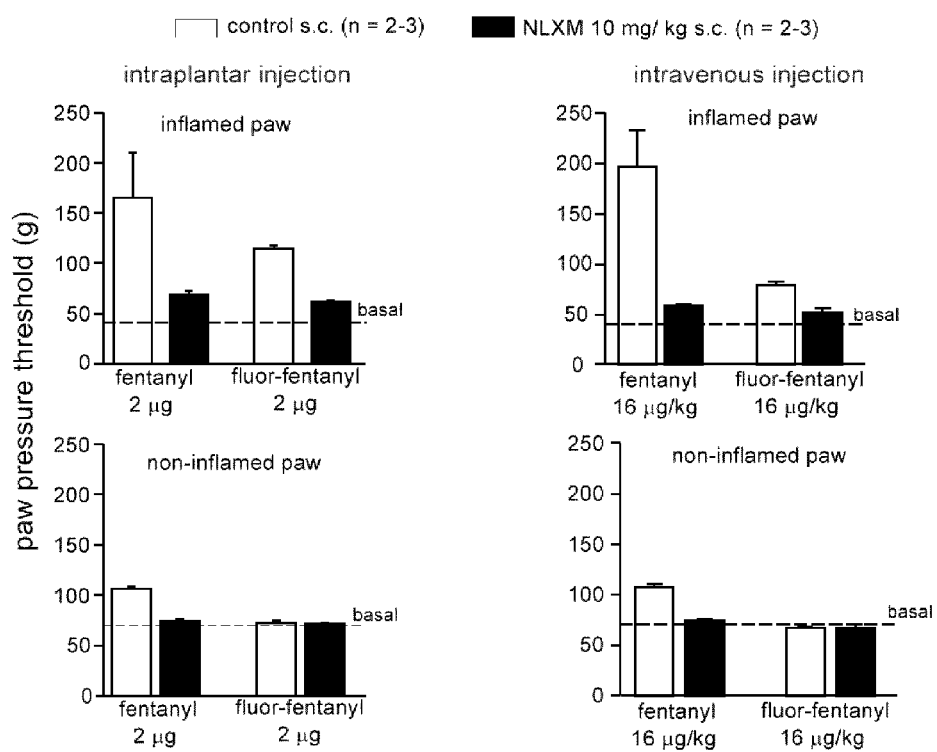

FIG. 7. Analgesic effect of fluor-fentanyl is blocked by naloxone methiodide (NLXM). Fluor-fentanyl produces analgesia only in inflamed paws. This effect is mediated by peripheral opioid receptors (i.e. blocked by the peripherally restricted opioid receptor antagonist NLXM).

Figure 8:
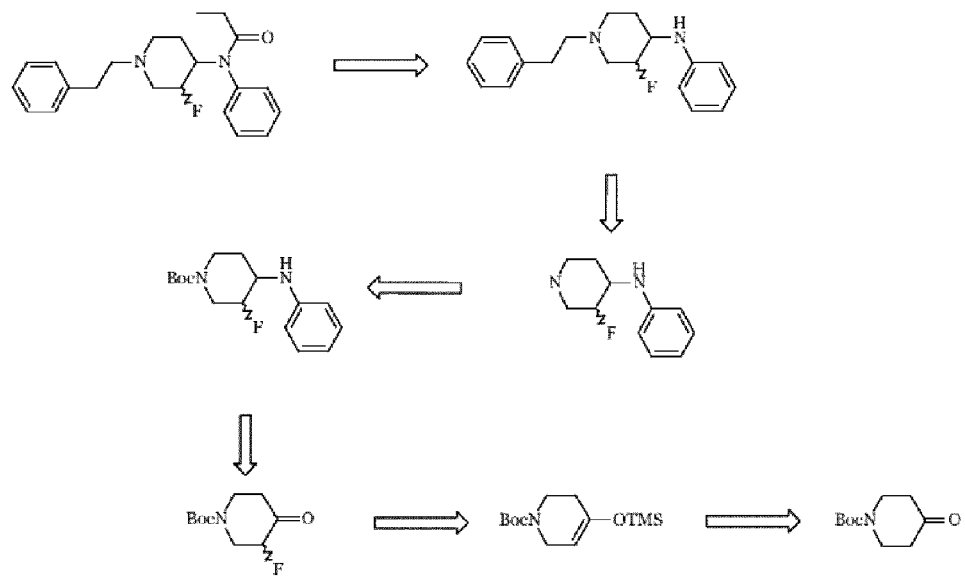
Figure 8:
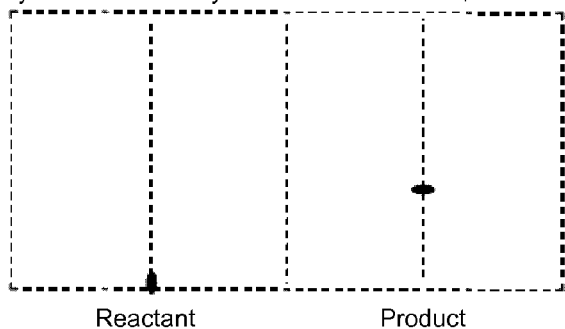
Figure 8:
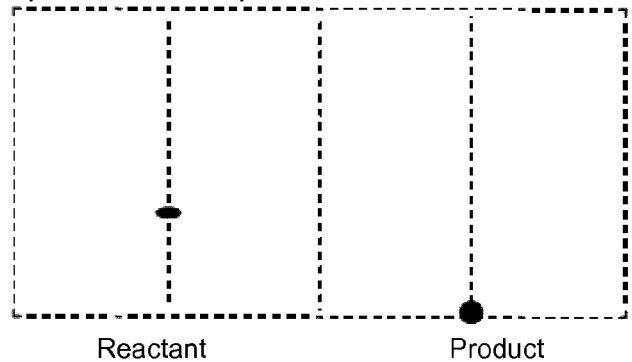
Figure 8:
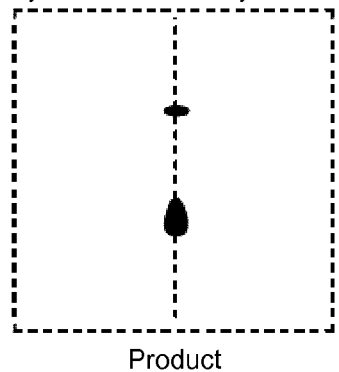
Figure 8:
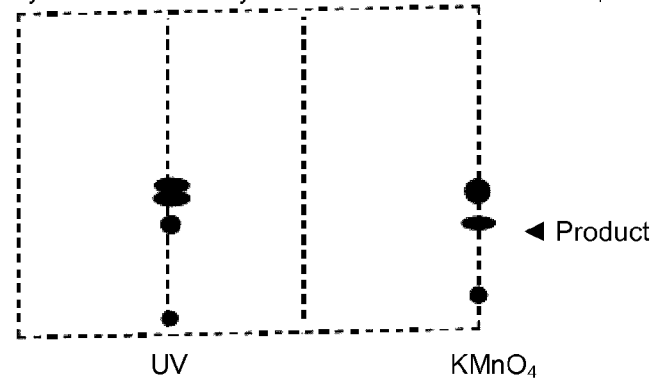
Figure 8:
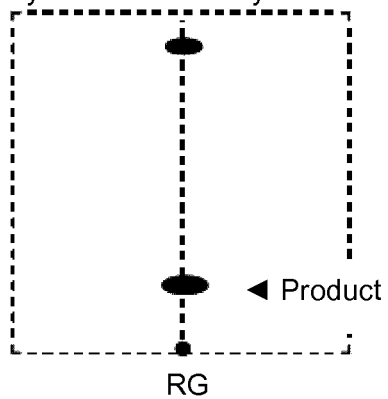
Figure 8:
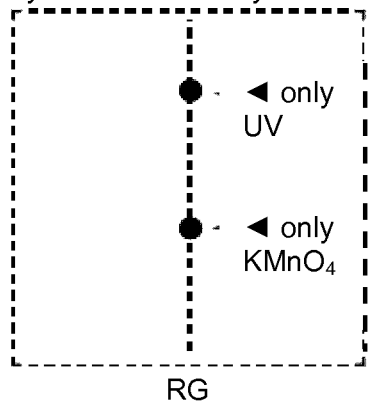

FIG. 8. Chemical synthesis of fluoro-fentanyl (F-fentanyl; (±)-N-(3-Fluor-1-phenethylpiperin-4-yl)-N-phenylpropionamide). An outline is provided of the synthesis scheme in addition to diagrams of the chromatographic separations of both the precursor and final compounds used and/or obtained during chemical synthesis.

EXAMPLES

The invention is further described by the following examples. These are not intended to limit the scope of the invention. The experimental examples relate to various in vitro experiments using cell culture, in addition to treatment of rats using unilateral hindpaw inflammation induced by intraplantar (i.pl.) injection in addition to intravenous (i.v.) injection. The rats represent a mammal model, used to demonstrate the invention by way of example. Other mammals, preferably humans, can also be treated by the method of the present invention.

Example 1

Synthesis of F-Fentanyl

The synthesis of fluoro-fentanyl (F-fentanyl; (±)-N-(3-Fluor-1-phenethylpiperin-4-yl)-N-phenylpropionamide) was carried out according to the following:

Step 1: Production of a Silyl Enol Ether

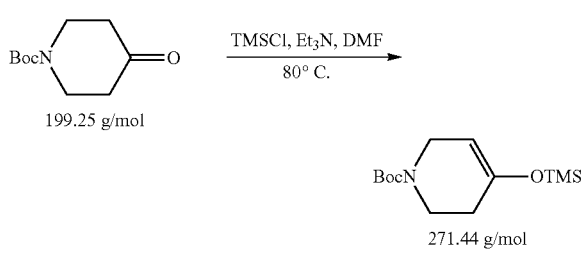

The reactant (3 g; 15.056 mmol; 1 eq) was dissolved in dry DMF under Argon and was subsequently mixed with triethylamine (1953 mg; 18.079 mmol; 2.4 eq) and chlortrimethylsilane (5 mL; 36.134 mmol; 1.2 eq), one after the other. The reaction ran for 16 hours at 80 deg C. The reaction mixture was transferred to a separating funnel with cyclohexane (100 ml) and washed 3 times with sodium hydrogen carbonate solution (3×40 ml). After drying over magnesium sulphate and concentrating under vacuum, the product is rinsed 4 times with toluene in order to completely remove the DMF. A yellow-brown oil is obtained.

Step 2: Fluorination

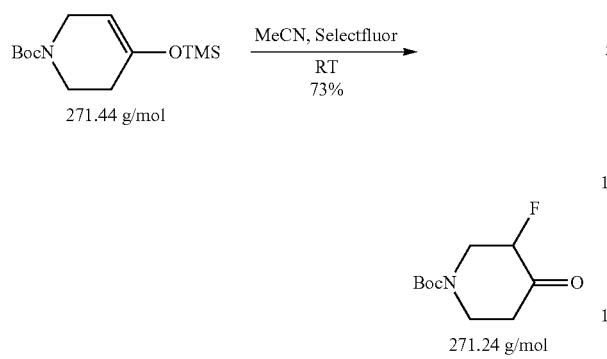

The raw product from step 1 (2566 mg; 9.453 mmol; 1 eq) was dissolved under Argon in dry acetonitrile and mixed with Selectfluor (a commercially available fluorine donor (1-Chloromethyl-4-fluoro-1,4-diazoniabicyclo[2.2.2]octane bis(tetrafluoroborate))) (3681 mg; 10.397 mmol; 1.1 eq). After 60 minutes shaking at room temperature the reaction mixture was transferred with ethylacetate (250 ml) to a separating funnel and first washed with diluted (2×75 ml) and afterwards with saturated NaCl-solution (80 ml). The organic phase was dried over magnesium sulphate and subsequently concentrated under vacuum. The obtained product is clean without requiring any further purification steps. A light brown resin is obtained.

Step 3: Reductive Amination

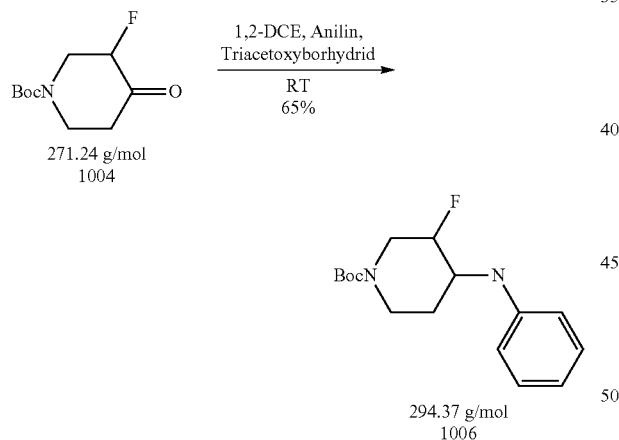

The fluorinated compound (1410 mg; 6.491 mmol; 1 eq) was presented with Anilin (0.65 mL; 7.140 mmol; 1.1 eq) and sodium triacetoxyborhydrid (2064 mg; 9.737 mmol; 1.5 eq) and dissolved under Argon in dry 1,2-dichloroethane. The reaction took 18 hours at room temperature. The reaction mixture was transferred with sodium hydrogen carbonate solution (70 ml) to a separating funnel and extracted with ethylacetate (2×70 ml). The combined organic phases were dried over magnesium sulphate and concentrated. Subsequently the product was purified by column chromatography (silica gel 60; cyclohexane/ethylacetate 19:1 (1500 mL), 15:1 (800 mL), 10:1 (2200 mL)). A colourless solid product was obtained.

Step 4: Removal of the Protecting Group

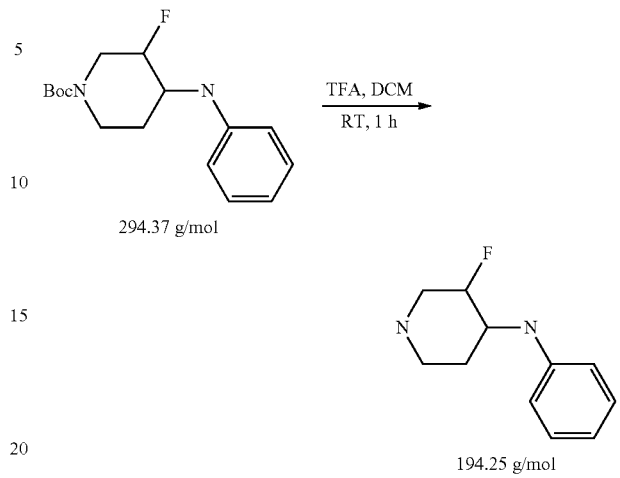

The product (824 mg; 2.799 mmol; 1 eq) was dissolved in a mixture of dichloromethane and trifluoroacetic acid (ratio of 2:1, 9 ml) and shaken for 1 hour at room temperature. Subsequently all liquid was removed under vacuum, so that a brown oil was obtained. The oil was transferred with methanol (2×20 ml) to a separating funnel. Distilled water (40 ml), 5 N caustic soda (8 ml) and saturated sodium chloride solution (30 ml) were added. Subsequently the product was extracted with ethylacetate (2×100 ml). Water and diethyl ether were added as long as needed until a phase separation occurred. The combined organic phases were dried over magnesium sulphate and subsequently dried under vacuum, so that a brown resin was obtained.

Step 5: Alkylation

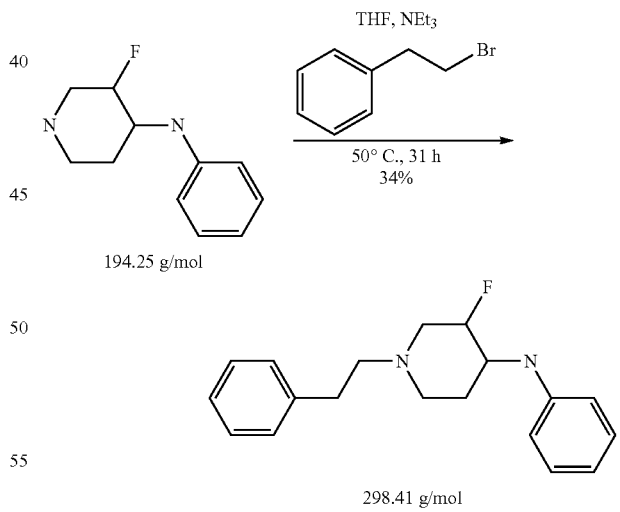

The resin from Step 5 (1198 mg; 6.167 mmol; 1 eq) was dissolved under Argon in dry THF (80 ml). Subsequently triethylamine (1.71 mL; 12.335 mmol; 2 eq) and phenethylbromide (2.50 mL; 18.501 mL; 3 eq) were added. The reaction took 30 hours at 50 deg C. Afterwards the reaction mixture was transferred with ethylacetate (250 ml) to a separating funnel and washed with sodium hydrogen carbonate solution (2×100 ml). The organic phase was dried over magnesium sulphate and concentrated under vacuum, so that a brown oil is obtained. The product was purified by column chromatography (silica gel 60; cyclohexane/ethylacetate 10:1 (1320 mL), 5:1 (300 mL), 3:1 (2100 mL). After purification a colourless solid was obtained.

Step 6: Acylation

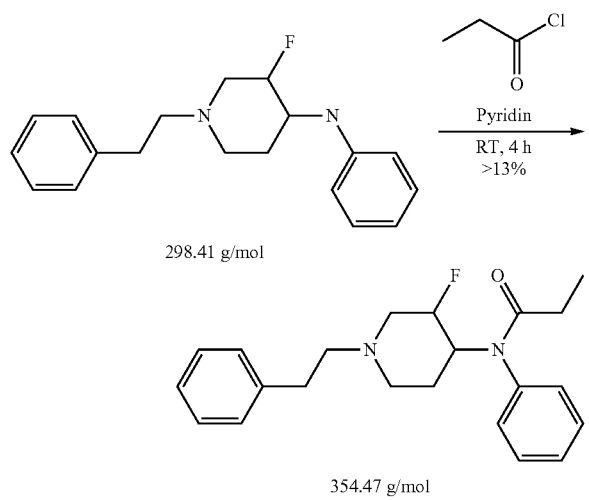

The product (661 mg; 2.215 mmol; 1 eq) was dissolved in Pyridin (35 ml) and while shaking mixed with propionylchloride (0.59 mL; 6.756 mmol; 3 eq). The reaction took 4 hours at room temperature and subsequently the reaction mixture was transferred with chloroform (2×50 ml) to a separating funnel and washed with distilled water (60 ml). A colourless solid precipitated which was separated with a frit and discarded. The organic phase was again washed with distilled water (50 ml). The product was purified by column chromatography (silica gel 60; cyclohexane/ethylacetate 4:1 (2650 mL), 3:1 (800 mL), 1:1 (400 mL), ethylacetate (250 mL)). The fractions, which only contained product, were concentrated, so that a yellow oil was obtained. The oil was resuspended in diethylether and via addition of n-pentane a light yellow solid product was precipitated.

An outline of the synthesis and results of the compound separation is demonstrated in FIG. 5.

In a preferred embodiment, the synthesis of F-fentanyl as described herein leads to a stereoisomeric mixture of the fluoro-fentanyl derivatives described by Formula I, in particular any given combination of two or more of the derivatives described by Formulae II to V, which exhibits the inventive properties of the present invention.

It is also within the abilities of a skilled practitioner to produce a fluor-fentanyl derivative with more than one F atom attached to one or more of the derivatized positions of the fentanyl backbone according to general formula I. Procedures for additional fluorination, for example on meta positions, are known and a skilled person is sufficiently equipped through his knowledge of common synthesis techniques to produce the claimed compounds.

Example 2

Structural and Physical Characteristics of F-Fentanyl

The synthesized compound had a formula of $C_{22}H_{27}FN_2O$, with a molecular weight of 354.47 g/mol and melting temperature of 110-114 deg C.

The structure of the fluoro-fentanyl (F-fentanyl, (±)-N-(3-Fluor-1-phenethylpiperin-4-yl)-N-phenylpropionamide) compound synthesized as described above was determined using liquid chromatography coupled with mass spectrometry (LCMS), and $^1H$, $^{13}C$ and $^{19}F$ spectra were obtained using NMR for the desired product.

$^1H$ NMR (CDCl$_3$): δ 7.433, 7.366, 7.354, 7.296, 7.275, 7.260, 7.213, 7.188, 7.167, 7.049, 5.270, 5.146, 4.635, 4.602, 4.553, 4.527, 3.343, 3.018, 2.991, 2.767, 2.626, 2.464, 2.429, 2.370, 2.336, 2.225, 1.996, 1.605, 1.583, 1.529, 1.511, 1.444, 1.416, 1.214, 1.035 ppm.

$^{13}C$ NMR (CDCl$_3$): δ 174.404, 139.978, 139.323, 131.231, 131.151, 130.157, 129.381, 128.626, 128.529, 128.392, 128.193, 126.073, 88.831, 87.064, 59.968, 56.060, 55.881, 55.060, 55.881, 55.061, 54.879, 52.505, 33.408, 28.552, 25.548, 9.464 ppm.

$^{19}F$ NMR (CDCl$_3$): δ 197.809 ppm.

Example 3

Mu-Opioid Receptor Function In Vitro

We used transfected HEK-293 cells and cultured dorsal root ganglion (DRG) neurons to examine mu-agonist binding, GTPγS binding, cAMP formation and modulation of TRPV1 currents by mu-agonists. Incubation of HEK-293 cells at different pH-values was initiated after the expression of mu-opioid receptors at the membrane surface was completed and stable. Affinity and number of mu-ligand ($^3H$-DAMGO) binding sites were slightly (nonsignificantly) lower at pH 5.5 compared to pH 7.5 (Tab. 1). Preincubation with the adenylyl cyclase activator forskolin (FSK; 10 μM) and the phosphodiesterase inhibitor 3-isobotyl-1-methylxanthin (IBMX; 2 mM) (control groups representing 100% cAMP accumulation compared to unstimulated cells) yielded no significant differences between pH values of 5.0, 6.0, 7.0 and 7.5 (FIG. 1). However, suppression of FSK/IBMX-stimulated cAMP formation by DAMGO and morphine was markedly stronger at pH 5.0 than at pH 7.5 (Tab. 1), indicating a higher efficacy of mu-agonist-induced inhibition of adenylyl cyclase activity in acidic conditions.

TABLE 1

Wild-type mu-receptors: mu-agonist binding and cAMP inhibition.

| pH | $^3H$-DAMGO $K_d$ (nM) | $^3H$-DAMGO $B_{max}$ (fmol/mg) | pH | 10 μM DAMGO cAMP (% baseline) | 10 μM Morphine |
|---|---|---|---|---|---|
| 5.5 | 5.561 | 14.04 | 5.0 | 43 ± 6 | 46 ± 11 |
| 6.5 | 2.101 | 15.50 | 6.5 | 68 ± 9 | 64 ± 13 |
| 7.5 | 1.149 | 23.95 | 7.5 | 82 ± 7 | 80 ± 10 |

Using fluoro-fentanyl (F-fentanyl, as synthesized in the methods provided herein) or fentanyl as mu-opioid receptor ligands the following results were obtained: Competitive binding experiments were performed using a fixed concentration of $^3H$-DAMGO (4 nM) in the presence of increasing concentrations ($10^{-6}$-1 μM) of unlabeled F-fentanyl and the half maximal inhibitory concentration (IC$_{50}$) was calculated. The resulting IC50 values were 1.03 nM (pH 5.5), 4.78 nM (pH 6.5) and 139.7 nM (pH 7.5), indicating that F-fentanyl displayed increasing affinity to mu-receptors with decreasing pH values. Thus, the lower the IC$_{50}$, the higher is the affinity of F-fentanyl to the mu-receptor (see also FIG. 1).

Both F-fentanyl and fentanyl produced significantly stronger reductions of FSK/IBMX-stimulated cAMP at pH 5.0 and 6.0 compared to pH 7.5 (FIG. 2). The difference between cAMP values at pH 5.0 and pH 7.5 seemed to be more pronounced for F-fentanyl than for fentanyl (F-fentanyl: **p=0.0011; fentanyl: *p=0.0118; ANOVA; FIG. 2). This demonstrates that F-fentanyl activates mu-opioid receptors predominantly during acidic conditions and is more effective than fentanyl.

We also assessed G-protein activation following mu-receptor activation by 35S-GTPγS-binding. F-fentanyl yielded half maximal effective concentrations (EC50) of 0.25 nM (pH 5.5) and 4.14 nM (pH 7.5). The corresponding values for fentanyl were 53.37 nM (pH 5.5) and 41.91 nM (pH 7.5). Thus, F-fentanyl was more potent at pH 5.5 than at pH 7.5, and it was more potent than fentanyl at all pH values.

Example 4

Antinociceptive Effects of Opioid Ligands In Vivo

In rats with unilateral hindpaw inflammation induced by intraplantar (i.pl.) Freund's complete adjuvant, fentanyl and F-fentanyl were injected either i.pl. into the inflamed paw or intravenously (i.v.) Paw pressure threshold (PPT) was used as a quantitative measure, whereby the test is based on determination of the animal's response threshold to withdraw the limb upon pain induced by the application of a uniformly increasing pressure to the paw.

At doses up to 1 µg, both drugs produced dose-dependent PPT elevations (antinociceptive effects) in the inflamed but not in the contralateral noninflamed paw. The effects of F-fentanyl were slightly stronger (FIG. 3). Consistent with our previous studies, this indicates that both drugs activate peripheral opioid receptors in inflamed but not in noninflamed tissue (FIG. 3). At higher doses (1.5-2 µg) fentanyl produced effects also on the contralateral paw, suggesting that the drug was absorbed into the circulation and produced antinociceptive effects mediated in the CNS (FIG. 3). This was not the case for F-fentanyl (FIG. 3), indicating that, even if the drug reached the CNS after absorption into the circulation, it did not activate central opioid receptors. Time course experiments with i.pl. administration reveal selective antinociception in the inflamed paw for F-fentanyl, demonstrating the inflammation-dependent effect of the F-fentanyl derivatives (FIG. 4).

The intravenous (i.v.) injection of high doses (32 µg/kg) was lethal in the case of fentanyl (due to central respiratory depression). The same i.v. dose of F-fentanyl did not elicit any noticeable central effects but produced selective antinociception in the inflamed paw (FIG. 5). This indicates that peripheral opioid receptors in the injured tissue but no central receptors were activated. Time course experiments with i.v. administration also reveal selective antinociception in the inflamed paw for F-fentanyl, demonstrating the inflammation-dependent effect of the F-fentanyl derivatives (FIG. 6).

Further experimentation using the peripherally-restricted opioid receptor blocker naloxone methiodide (NLXM), which does not permeate the blood brain barrier and hence does not enter the CNS, shows that F-fentanyl, which produces analgesia only in inflamed paws, is mediated by peripheral opioid receptors (FIG. 7).

Additional experimentation can demonstrate that the fluor-fentanyl compounds of the present invention exhibit the above-shown effects in direct comparison to known fentanyl derivatives of the prior art, for example methyl-fentanyl, which due to their disadvantageous pKa values are not appropriate for producing pH-specific effects. The clear differences in electronegativity between methyl and fluor lead one skilled in the art to recognise that methyl-fentanyl derivatives will not produce the desired effect described herein.

Methods Used In The Examples Of The Present Invention

Cell culture and transfection: HEK293 cells are maintained in DMEM media supplemented with 10% fetal bovine serum and 1% streptomycin-penicillin, in 5% CO2 at 37° C. Cells are passaged every 2-4 days and are not used above passage number 30. HEK293 cells are plated on poly-L-lysine-coated 96 well plates for ELISA and on 100 mm diameter plastic culture dishes for binding studies. After 2 days HEK293 cells are transiently transfected with 12 µg (binding experiments) and 0.1 µg (ELISA experiments) cDNAs of rat wildtype or mutant mu-opioid receptor using FuGENE 6 Transfection Reagent (Roche Diagnostics). Twenty four h after transfection, cells are preincubated at room temperature for 20 min at varying pH values (5.5-7.4) and then processed for further experiments.

Cyclic AMP enzyme linked immunosorbent assay (ELISA): Transfected cells are cultivated in a 96-well-plate and incubated with 10 µM forskolin, 2 mM 3-Isobutyl-1-methyl-Xanthin (IBMX) in the absence or presence of morphine/DAMGO under different pH conditions (5.0; 5.5; 6.0; 6.5; 7.0; 7.4) for min 20 min at 37° C. cAMP measurements are performed using the cAMP Biotrak Enzymeimmunoassay System (Amersham Biosciences) protocol following the manufacturer's instructions. Non-bound cAMP peroxidase oxidizes tetramethylbenzidine to a blue derivate. The reaction is stopped by applying sulphuric acid resulting in the accumulation of a yellow dye. The intensity of the color is detected with an ELISA-photometer at 450 nm.

Ligand binding: Membranes of HEK 293 cells expressing mu-opioid receptors are washed twice with 10 ml of Tris buffer (Trizma Preset Crystals pH 7.4; Sigma), harvested with a scraper, homogenized and centrifuged at 42000 g and 4° C. for 20 min. The pellet is homogenized in 10 ml Tris and centrifuged at 42000g and 4° C. for 20 min. Protein concentration is determined using the Bradford method. Appropriate concentrations of cell membranes (200 µg) are incubated in a final volume of 400 µl Tris buffer (pH 5.5, 6.5 or 7.4) with increasing concentrations of e.g. 3H-DAMGO (0.5 nM-16 nM) (51Ci/mmol; Amersham) (or other ligands) in the absence and presence of 10 µM unlabeled naloxone. The presence of naloxone defines non-specific binding, which typically represents 15 to 35% of total binding. Filters are soaked in 0.1% (w/v) polyethyleneimine solution for 15 min before using. Bound and free ligand are separated by rapid filtration under vacuum through Whatman GF/B glass fiber filters, followed by four washes with cold Tris buffer. Bound radioactivity is determined by liquid scintillation spectrophotometry at 69% counting efficiency for 3H after overnight extraction of the filters in 3 ml of scintillation fluid.

Guanosine-5'-O-(3-$^{35}$S-thio)-triphosphate ($^{35}$S-GTPγS) binding: After preincubation for 20 min at varying pH values (5.5-7.4), HEK 293 cells expressing wild-type or mutant mu-opioid receptors are washed two times with 10 ml PBS, harvested with a scraper in 10 ml $^{35}$S-GTPγS assay buffer (50 mM Tris-HCL, 5 mM MgCl$_2$, 0.2 mM EGTA, 100 mM NaCl, and 1 mM dithiothreitol), homogenized and centrifuged at 42000 g and 4° C. for 10 min. Cell pellets are resuspended in 10 ml $^{35}$S-GTPγS assay buffer, homogenized and centrifuged again. Protein concentration is measured using the Bradford method. Adequate concentrations of protein (10-50 μg), varying concentrations of DAMGO ($10^{-12}$-$10^{-4}$ M) (or other ligands), 50 μM GDP and 0.05 nM$^{35}$S-GTPγS in a total volume of 800 μl are incubated for 2 h to generate concentration-effect curves. Basal binding is detected in the absence of agonist and non-specific binding in the presence of 10 μM cold GTPγS. Bound and free $^{35}$S-GTPγS are separated by vacuum filtration through GF/B filters. Quantification of bound $^{35}$S-GTPγS is achieved by a liquid scintillation counter. Similar to our previous studies, saturation analysis of mu-agonist-stimulated GTPγS binding is performed to determine the $K_d$ of GTPγS and the total amount ($B_{max}$) of G-protein binding to the mu-receptor. Similar experiments are performed in DRG membranes obtained from the inflamed or noninflamed limbs of animals treated with intraplantar CFA, as commonly carried out in the art.

The invention claimed is:

1. Compound of Formula I, or a salt thereof:

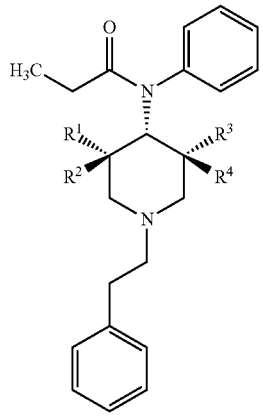

Formula I wherein one of $R^1$, $R^2$, $R^3$ or $R^4$ is F, and the remaining residues at positions $R^1$, $R^2$, $R^3$ and $R^4$ are H.

2. Compound according to claim 1, selected from the group consisting of:

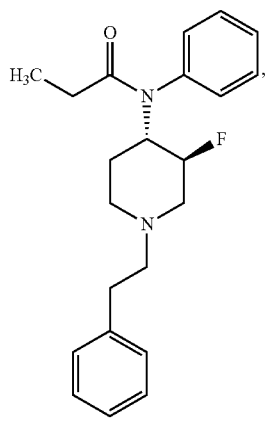

Formula II

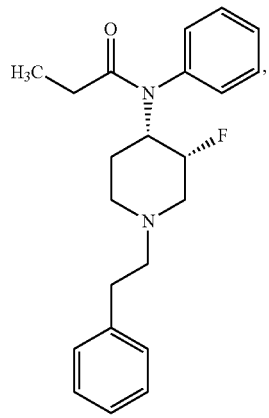

Formula III

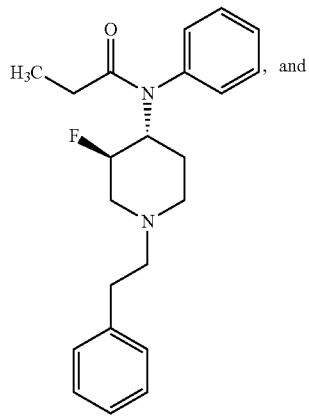

Formula IV

, and

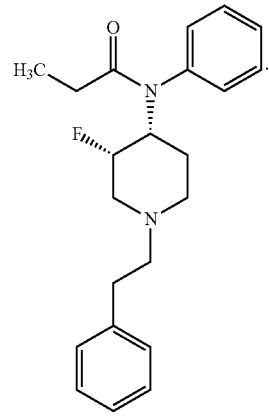

Formula V

3. Pharmaceutical composition comprising the compound according to claim 1, and/or a salt, and/or stereoisomer thereof, together with at least one pharmaceutically acceptable carrier.

4. Pharmaceutical composition according to claim 3, comprising a mixture of at least 2 compounds according to formulae II, III, IV and/or V,and/or salts, derivatives and/or stereoisomers thereof.

5. Pharmaceutical composition according to claim 3 formulated for systemic, oral, topical and/or local application.

6. The pharmaceutical composition according to claim 4, comprising a stereoisomeric mixture of compounds according to formulae II, III, IV and/or V.

7. Pharmaceutical composition according to claim 5 in tablet form or in a form suitable for injection.

8. A method of treating inflammation-associated pain comprising administering to a subject a compound according to claim 1.

9. The method of claim 8, wherein said inflammation-associated pain is selected from the group consisting of arthritis, skin inflammation, inflammatory back pain, headache, neurogenic migraine, inflammatory lesions of the central and peripheral nervous system, neuropathic pain, cancer pain, disorders of the immune system, HIV/AIDS, multiple sclerosis, traumatic pain, postoperative pain, inflamed joints, dental surgery, visceral pain, bone pain, burn injury and eye lesions.

* * * * *